United States Patent [19]

Grieshaber et al.

[11] Patent Number: 5,716,328
[45] Date of Patent: Feb. 10, 1998

[54] IRIS RETRACTOR FOR USE IN SURGICAL PROCEDURE ON THE EYE OF A LIVING BEING

[75] Inventors: Hans R. Grieshaber, Schaffhausen, Switzerland; Kazuaki Kadonosono, Yokohama, Japan

[73] Assignee: Grieshaber & Co. AG Schaffhausen, Schaffhausen, Switzerland

[21] Appl. No.: 794,320

[22] Filed: Feb. 3, 1997

[30] Foreign Application Priority Data

Aug. 7, 1996 [CH] Switzerland .............. 19961934/96

[51] Int. Cl.$^6$ .............................. A61B 17/02
[52] U.S. Cl. .............. 600/206; 600/227; 600/236
[58] Field of Search ................... 600/201, 206, 600/208, 209, 227, 235, 236

[56] References Cited

U.S. PATENT DOCUMENTS

| | | |
|---|---|---|
| 4,190,042 | 2/1980 | Sinnreich .................. 600/206 X |
| 4,428,746 | 1/1984 | Mendez ..................... 600/209 X |
| 5,174,279 | 12/1992 | Cobo et al. ................ 600/236 X |
| 5,290,292 | 3/1994 | Householder ............. 600/236 X |
| 5,514,076 | 5/1996 | Ley ............................ 600/236 X |

*Primary Examiner*—Jeffrey A. Smith
*Attorney, Agent, or Firm*—Henry M. Feiereisen

[57] ABSTRACT

An iris retractor for use in ophthalmic surgery, includes an elongated body portion for insertion through an incision in the eye to retract the iris, with the body portion including two parallel shafts secured to each other along a common longitudinal edge wherein each shaft has at least one end formed with a hook-shaped member. The shafts of the body portion are so joined together that the hook-shaped members diverge from the longitudinal edge downward at an angle to one another to exhibit a Λ-shaped configuration, and exhibit parallel shanks which are spaced from each other at a distance, the dimension of which depends on the angle between the hook-shaped members.

12 Claims, 3 Drawing Sheets

IRIS RETRACTOR FOR USE IN SURGICAL PROCEDURE ON THE EYE OF A LIVING BEING

BACKGROUND OF THE INVENTION

The present invention generally refers to a surgical instrument for use in ophthalmic surgery, and in particular to an iris retractor for use in eye surgery of a living being for retraction of the iris.

Iris retractors are known which generally include an elongated body portion, an engagement member having a substantially hook-shaped configuration for retracting the iris, and a fixation member slidably mounted on the body portion for securing the iris retractor in place when the body portion is inserted with its hook-shaped end into the anterior chamber through a suitable incision made in the cornea.

It is well known that adequate dilation of the pupil of the eye is essential during e.g. cataract surgery. In particular, for removal of a cataract, the surgical procedure in the posterior section as well as anterior section of the eye requires a sufficiently large and constant viewing range for the surgeon. Generally, the dilation of the pupil is effected through administration of pharmaceuticals. However, on occasions, the use of pharmaceuticals is insufficient to attain the desired dilution so that the use of surgical instruments for retracting the iris is proposed, e.g. application of one or more suitably spaced iris retractors which attach to the iris to pull it outwardly for enlarging the opening of the pupil. The individual iris retractors are inserted into the anterior chamber of the eye through an incision in the cornea and suitably fixed in place at the eye by a fixation member. After surgery, the iris retractor is removed.

European Pat. No. EP-A 0 502 258 describes an iris retractor of the above type which includes a body portion with a hook-shaped engagement member, and a plate-shaped fixation member which is slidably mounted to the body portion. The fixation member is thus traversed by the body portion and is formed at least at the side facing the outer cornea contour with an arcuated recess for subdividing the fixation member in two pads to thereby match the outer cornea contour.

European Pat. No. EP-A 0 653 197 describes an iris retractor made of flexible, thermoplastic material and essentially including a body portion, a fixation member slidably mounted along the body portion, and an engagement member of arcuated configuration which is attached to one end of the body portion. Through heat treatment, the engagement member receives a limited stiffness to thereby enable a retraction of the iris while allowing a sufficient straightening thereof during withdrawal of the body portion from the eye.

SUMMARY OF THE INVENTION

It is an object of the present invention to provide an improved iris retractor which allows a retraction of a relatively large area of the iris without tearing of the iris and yet can be handled in a precise manner during insertion into the anterior chamber of the eye through a relatively small, self-sealing incision.

This object, and others which will become apparent hereinafter, are attained in accordance with the present invention by forming the body portion of the iris retractor of two shafts which are arranged parallel to each other and joined together along a longitudinal edge, with each shaft having at least one end exhibiting a hook-shaped member, wherein the hook-shaped members of the shafts are so positioned relative to each other as to diverge from the longitudinal edge downward at an angle to each other in a Λ-shaped configuration, with the hook-shaped members exhibiting parallel shanks which are spaced from each other at a distance that depends on the angle between the hook-shaped members, and by slidably securing a fixation member to the body portion for positioning and securing the body portion in place.

Preferably, the angle defined by the hook-shaped members is an acute angle ranging between about 30° to 60°.

According to another feature of the present invention, each shaft is made of a flexible thermoplastic suture material, preferably polyamide, with the hook-shaped member being formed onto the shaft through a heat treatment process that affords the hook-shaped members with a limited, localized stiffness with relative slight resistance so as to enable a straightening thereof during withdrawal from the eye and return to the hook-shaped configuration as a result of its own spring-elastic return action.

According to another feature of the present invention, the fixation member is formed with two opposite bores in spaced-apart relationship for attachment on the shafts and displacement in a longitudinal direction while being secured against rotation. Preferably, the fixation member is of disk-like configuration and made of a transparent silicone rubber, with the two bores exhibiting a profile substantially matching the profile of the shafts which are preferably of circular configuration.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
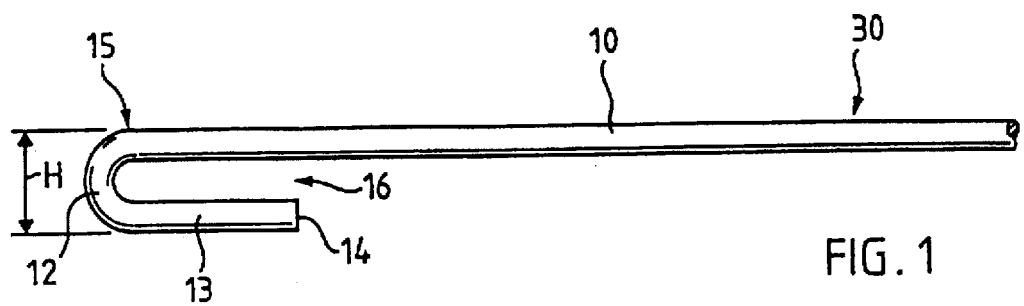
FIG. 1 is a side view, on an enlarged scale, of one embodiment of a body portion of an iris retractor according to the present invention.

Throughout all the Figures, the same or corresponding elements are generally indicated by the same reference numerals.

Figure 3:
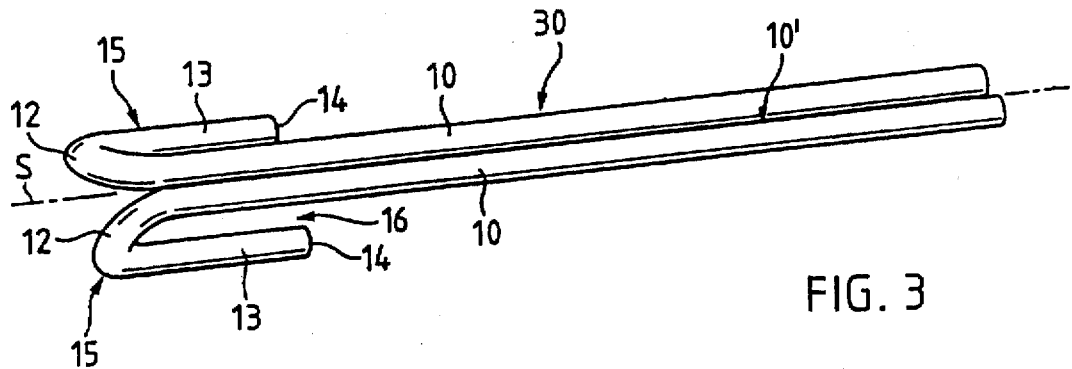
FIG. 3 is a perspective illustration of the body portion of FIG. 1 from above.
Figure 4:
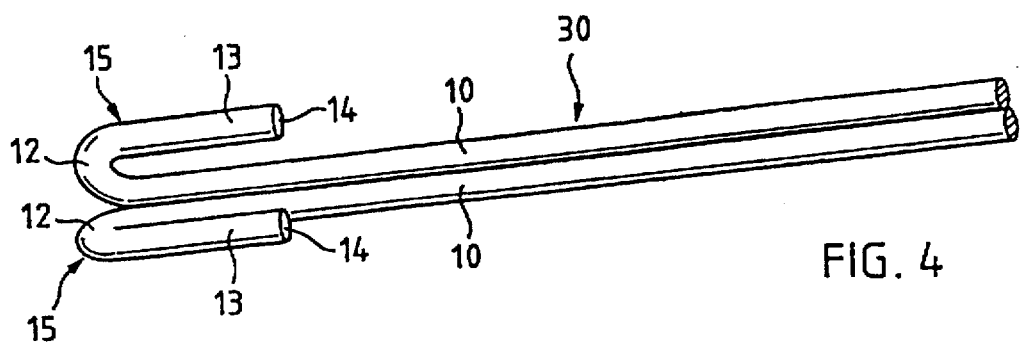
FIG. 4 is a perspective illustration of the body portion of FIG. 1 from below in direction of arrow IV in FIG. 2.
Figure 5:
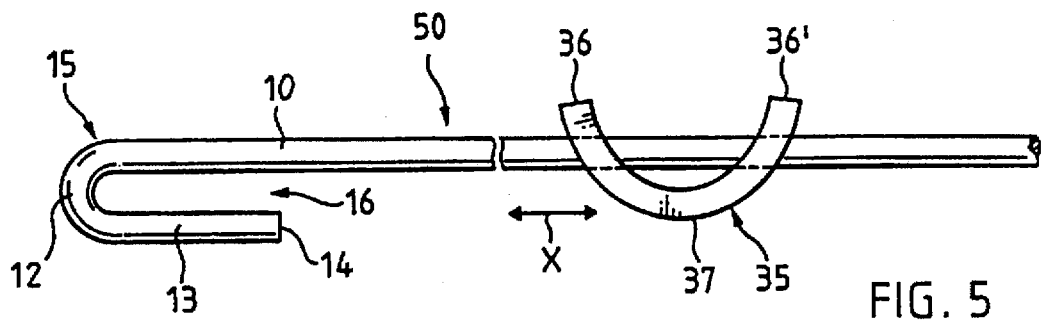
FIG. 5 is a side view of an iris retractor according to the present invention, comprised of body portion and fixation member.

Turning now to the drawing, and in particular to FIGS. 1 to 4, there are shown various views, on an enlarged scale, of one embodiment of a body portion, generally designated by reference numeral 30 and forming part of an iris retractor, as shown in FIG. 5, for use in a surgical procedure on the eye of a living being. The body portion 30 includes two substantially elongated shafts 10 (e.g. FIG. 2) which extend parallel to one another and terminate in engagement members, generally designated by reference numeral 15 and exhibiting a hook-shaped configuration. The shafts 10 are of identical configuration and suitably joined together, e.g. by an adhesive, along a longitudinal edge 10' which coincides with an axis of symmetry S.

The shafts 10 are made of suture material exhibiting a smooth surface, with the hook-shaped member 15 of each shaft 10 including an arched portion 12 and a shank 13 which extends rearwardly from the arched portion 12, and defined by an overall height H. The shank 13 extends parallel to the shaft 10 at a distance 16 thereto and terminates in a vertical end face 14. Thus, each hook-shaped member 15 of the body portion 30 exhibits a U-shaped or hairpin configuration. It will be understood by persons skilled in the art that the end face 14 may certainly be formed of rounded configuration.

Figure 2:
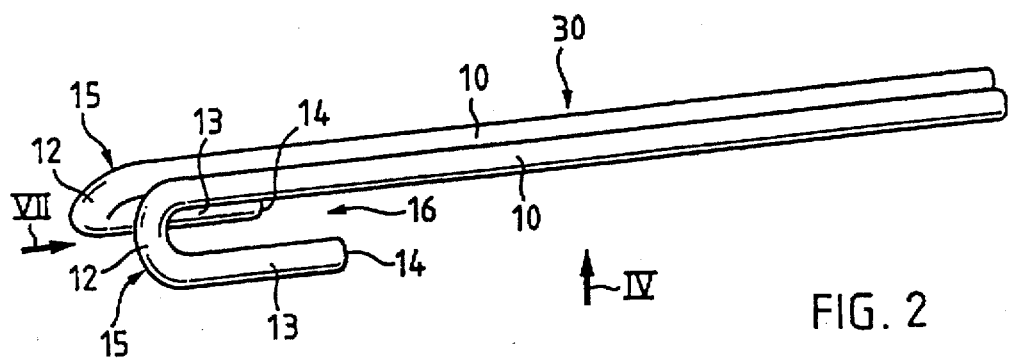
FIG. 2 is a perspective illustration of the body portion of FIG. 1.
Figure 7:
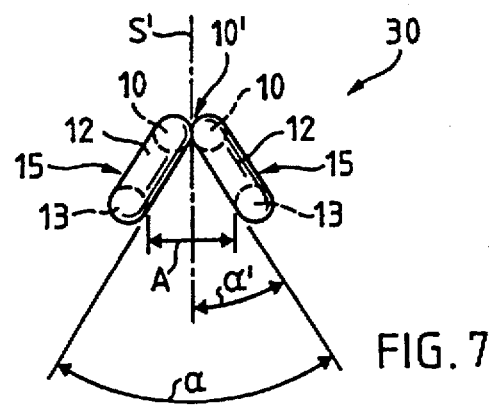
FIG. 7 is a front view of the body portion of FIG. 2, as viewed in direction of arrow VII in FIG. 2.

As best seen in FIGS. 2 to 4 in combination with FIG. 7, which shows a front view of the body portion 30 as viewed in direction of arrow VII in FIG. 2, the hook-shaped members 15 of the body portion 30 are arranged at an acute angle $\alpha$ to one another to exhibit a downwardly diverging substantially $\Lambda$-shaped configuration. The shanks 13 extend rearwardly in parallel relationship from the arched sections 12 and are spaced from one another by a distance A, the dimension of which depends on the magnitude of the angle $\alpha$. The shafts 10 of the body portion 30 are so positioned and joined together along the axis of symmetry S that the acute angle $\alpha$ ranges between 30° to 60°.

In accordance with a variation of the present invention, one hook-shaped member 15 may be positioned in direction of a vertical axis S', with the other hook-shaped member 15 extending an at an angle $\alpha'$ thereto, as also indicated in FIG. 7.

Figure 6:
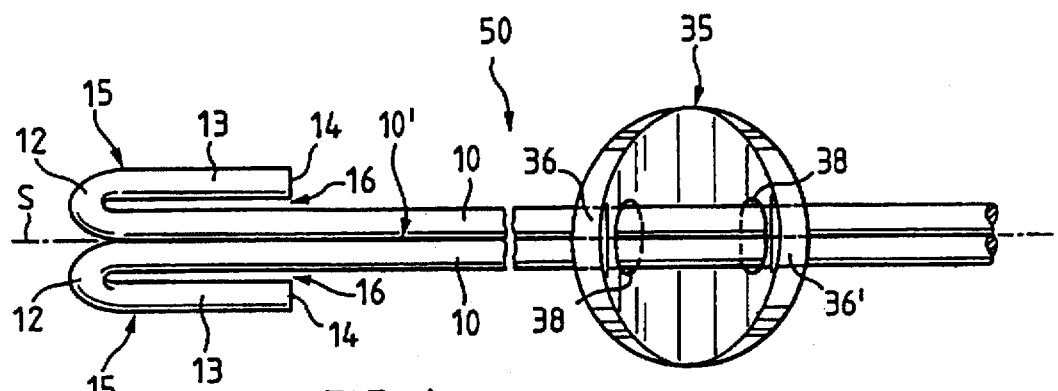
FIG. 6 is a top view of the iris retractor of FIG. 5.

Turning now to FIGS. 5 and 6, there are shown a side view and a plan view of an iris retractor according to the present invention, generally designated by reference numeral 50 and incorporating the body portion 30, as shown in FIGS. 1-4, in combination with a fixation member, generally designated by reference numeral 35 and preferably configured in the form of a circular disk. The fixation member 35 is made of flexible material, which may be transparent e.g. silicone rubber, and includes two spaced bores 38 for receiving the shafts 10 and allowing displacement of the fixation member 35 along the shafts 10 in direction of double arrow X.

Upon placement on the shafts 10, the fixation member 35 exhibits on one side of the body portion 30 an arcuated seat surface 37, while exhibiting spaced projections 36, 36' on the other side of the body portion 30. In order to shift the fixation member 35 along both shafts 10 of the body portion 30, the projections 36, 36' are pressed in direction towards each other to position the bores 38 in such a manner that their inner circumferential edges essentially become disengaged from the shafts 10, so that the fixation member 35 can now easily be moved along the shafts 10. By releasing the projections 36, 36', the fixation member 35 snaps back and is secured in place in self-locking manner in the selected position on the shafts 10.

Suitably, the flexible plastic material affords the fixation member 35 with sufficient sliding properties so as to allow an easy displacement of the fixation member 35 along the shafts 10 when squeezing the projections 36, 36'.

Persons skilled in the art will understand that the bores 38 of the fixation member 35 are so dimensioned as to effect the self-locking action while allowing a displacement along the shafts 10 in direction of the double arrow X when suitably squeezing the fixation member 35 at the projections 36, 36'. Suitably, the bores 38 are so configured as to match the circular profile of both shafts 10.

Preferably, both shafts 10 are made of relatively flexible thermoplastic suture material, e.g. polyamide, so as to have surfaces which exhibit excellent sliding properties. The formation of the hook-shaped members 15 according to the configuration shown in FIG. 1 is effected through a heat treatment process which involves placement of the shafts 10 in a suitably shaped mold (not shown) which is then heated (malleableized) to form the hook-shaped members 15 and to afford a localized stiffness, whereas the shafts 10 which are relatively long in relation to the hook-shaped members 15, retain their flexibility to a large extent.

Following the heat treatment, the shanks 10 are so joined together along their entire length by a suitable adhesive that the angle $\alpha$ is described between the hook-shaped members 15.

Figure 8:
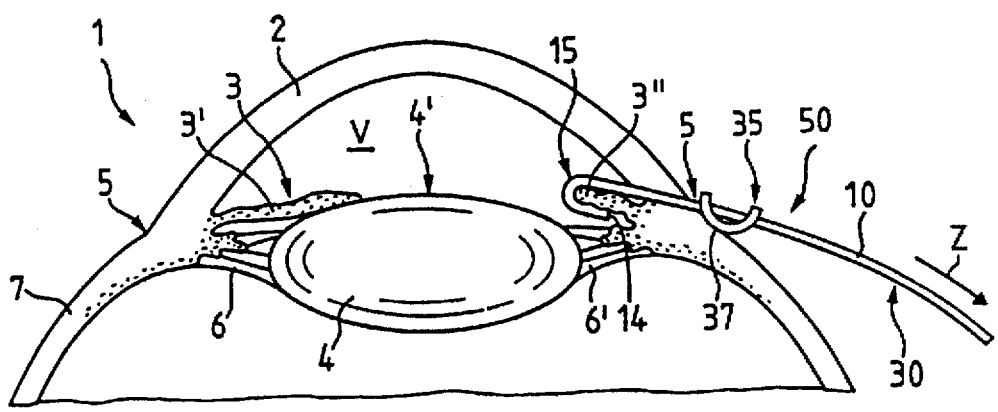
FIG. 8 is an enlarged schematic illustration of the forward eye section of a living being, illustrating one region of the iris being retracted by an iris retractor according to the present invention.

Turning now to FIG. 8, there is shown an enlarged schematic illustration of the forward eye section 1 of a living being, including the cornea 2, the iris generally designated by reference numeral 3 and including both circular areas 3', 3", the sclera 7, the lens 4 (ocular) with the ciliary processes 6, 6' (zonule fibers) and the pupil 4', and the anterior chamber designated in its entirety by reference character V. The iris retractor 50 is inserted through an incision in a transition area 5 between the cornea 2 and the sclera 7 and engages the circular area 3" of the iris 3, with the arcuated seat surface 37 of the fixation member 35 securing the iris retractor 50 in place by bearing upon the transition area 5. The flexible shafts 10 of the body portion 30 are of slightly curved configuration to substantially match the outer contour of the sclera 7. In this manner, even a placement of several, evenly spaced iris retractors 50 about the circular areas, results in a sufficiently accessible surgical site, and the surgeon will not get caught on protruding parts of the body portion 30 of the iris retractors 50. An unintentional contact of the body portion 30 by the surgeon is substantially compensated by the flexibility of the shafts 10 so that an unintentional bumping will not result in dangerous consequences for the eye such as ripping out the iris retractor or adversely affecting the lens.

Persons skilled in the art will understand that even though FIG. 8 shows the shafts 10 of arched configuration exhibiting a relatively great radius, it is certainly within the scope of the present invention to form the shafts 10 of substantially straight configuration.

Figure 9:
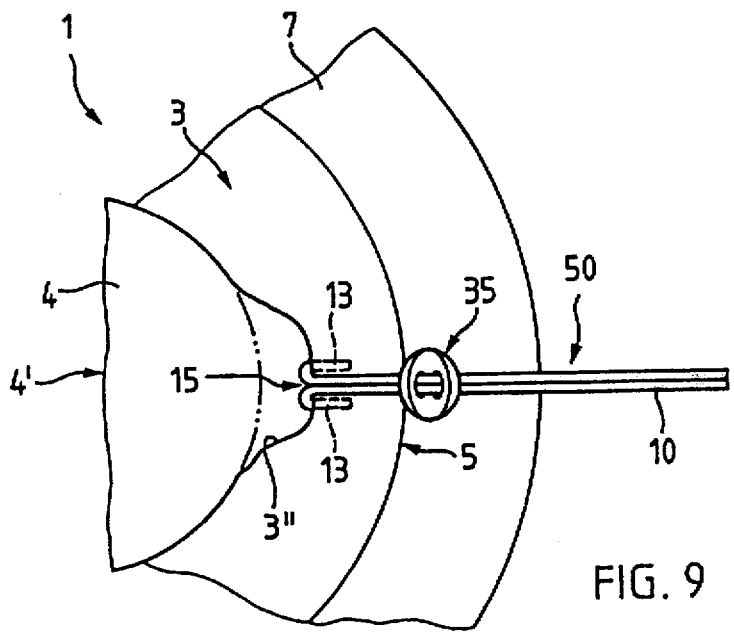
FIG. 9 is an enlarged, schematic plan view of a portion of the eye with partially retracted iris.

Referring now to FIG. 9, there is shown an enlarged schematic plan view of a portion of the eye 1, illustrating the partially retracted iris 3 through application of the iris retractor 50 according to the present invention, with the ring-shaped fixation member 35 being disposed at the transition area 5 of the sclera 7 and the cornea 2 for retaining the iris retractor 50 in place.

Figure 10:
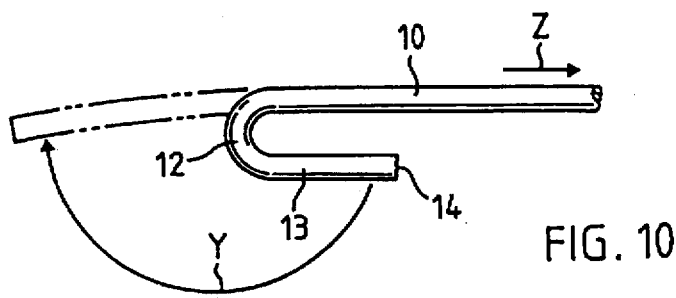
FIG. 10 is an enlarged side view of a forward section of the body portion of the iris retractor, with illustration, in dashdot lines, of a straightened configuration of the hook-shaped member during withdrawal of the iris retractor.

As described above, the heat treatment of the body portion 15 affords a localized stiffness in the area of the hook-shaped members 15 so that the arched portions 12, as schematically illustrated in FIG. 10, can be straightened in a direction indicated by arrow Y in opposition to the own spring-elastic return force when withdrawing the iris retractor 50 in a direction indicated by arrow Z. After withdrawal of the iris retractor 50, the inherent spring force urges the hook-shaped members 15 to return to their original configuration. Thus, the iris retractor 50 according to the present invention is suitable for repeated use.

The withdrawal of the iris retractor 50 is typically effected by initially turning the body portion 30 by an angle of about 70° to 90° about its axis of symmetry S, and then by pulling the iris retractor 50 in direction of arrow Z. As soon as the end faces 14 of the shanks 13 move up against the transition area 5 between the cornea 2 and the sclera 7, the hook-shaped members 15 are straightened as a consequence of the natural resistance of the transition area 5 so that the body portion 30 may easily be removed in direction of arrow Z, without any tearing and enlarging of the incision in the cornea 2. After withdrawal of the iris retractor 50, the incision in the cornea 2 seals itself.

The withdrawal of iris retractor 50 may however, also be effected by first retracting the fixation member 35 and then further pushing the body portion 30 in opposition to the arrow Z into the anterior chamber V. As soon as both hook-shaped members 15 are disengaged from the circular area 3" of the iris 3, the body portion 30 is turned by an angle of about 70° to 90° about its axis of symmetry S. Subsequently, the iris retractor 50 can be fully withdrawn in direction of arrow Z. After withdrawal of the iris retractor 50, the incision in the cornea 2 seals itself.

For ease of understanding, it is noted that the iris retractor 50 according to the present invention typically has an overall length of about 5 mm to 8 mm, with the length of the shanks 13 being in the range between 1.0 mm and 1.5 mm. The overall height H (FIG. 1) of the arched portions 12 ranges between about 0.4 mm and 0.5 mm. Suitably, the polyamide suture material for the shafts 10 is of circular cross section, defined by a diameter of about 0.15 mm to 0.2 mm.

While the invention has been illustrated and described as embodied in an iris retractor for use in surgical procedure on the eye of a living being, it is not intended to be limited to the details shown since various modifications and structural changes may be made without departing in any way from the spirit of the present invention.

What is claimed as new and desired to be protected by Letters Patent is set forth in the appended claims:

1. An instrument for use in ophthalmic surgery, comprising
   an elongated body portion for insertion through an incision in the eye to retract the iris, said body portion including two parallel shafts secured to each other along a common longitudinal edge and each having at least one end formed with a hook-shaped member, said hook-shaped members of the shafts diverging from the longitudinal edge downward at an angle to one another to exhibit a Λ-shaped configuration, and exhibiting parallel shanks spaced from each other at a distance, the dimension of which depends on the angle; and
   a fixation member slidably secured to the body portion for positioning and fixing the body portion in place.

2. The instrument of claim 1 wherein the angle between the hook-shaped members is an acute angle.

3. The instrument of claim 2 wherein the acute angle is in the range of about 30° to 60°.

4. The instrument of claim 1 wherein the shafts define a plane of symmetry and are so positioned relative to one another that the hook-shaped member of one shaft extends along a vertical axis perpendicular to the plane of symmetry, with the hook-shaped member of the other shaft being spaced to the hook-shaped member of the one shaft at an acute angle.

5. The instrument of claim 1 wherein the shafts exhibit a circular cross section, and further comprising connection means for securely fixing the shafts to one another along the longitudinal edge.

6. The instrument of claim 1 wherein each shaft is made of a flexible thermoplastic suture material, with the hook-shaped member being formed on the shaft through a heat treatment process.

7. The instrument of claim 6 wherein the suture material is made of polyamide.

8. The instrument of claim 6 wherein the hook-shaped members exhibit a limited, local stiffness with relative slight resistance for enabling a straightening thereof during withdrawal from the eye and return to a hook-shaped configuration as a result of their own spring-elastic return force.

9. The instrument of claim 1 wherein the fixation member is formed with two opposite bores in spaced-apart relationship and guided on the shafts for displacement in a longitudinal direction while secured against rotation.

10. The instrument of claim 9 wherein the fixation member is of disk-like configuration, with the two bores exhibiting a profile substantially matching a profile of the shafts.

11. The instrument of claim 10 wherein the shafts are of circular configuration.

12. The instrument of claim 1 wherein the fixation member is made of a transparent silicone rubber.

* * * * *